(12) United States Patent
Ren et al.

(10) Patent No.: US 11,306,365 B1
(45) Date of Patent: Apr. 19, 2022

(54) **MOLECULAR MARKER C42257 FOR RAPIDLY IDENTIFYING GENETIC SEX OF *MARSUPENAEUS JAPONICUS* AND APPLICATIONS THEREOF**

(71) Applicant: Yellow Sea Fisheries Research Institute, Chinese Academy of Fishery Sciences, Shandong (CN)

(72) Inventors: Xianyun Ren, Shandong (CN); Jianjian Lv, Shandong (CN); Weikang Lan, Shandong (CN); Ling Jin, Shandong (CN); Ping Liu, Shandong (CN); Jian Li, Shandong (CN)

(73) Assignee: Yellow Sea Fisheries Research Institute, Chinese Academy of Fishery Sciences, Qingdao (CN)

( * ) Notice: Subject to any disclaimer, the term of this patent is extended or adjusted under 35 U.S.C. 154(b) by 0 days.

(21) Appl. No.: 17/465,825

(22) Filed: Sep. 2, 2021

(30) Foreign Application Priority Data

Jul. 7, 2021 (CN) .......................... 202110765274.X

(51) Int. Cl.
*C12Q 1/68* (2018.01)
*C12Q 1/6888* (2018.01)

(52) U.S. Cl.
CPC ..... *C12Q 1/6888* (2013.01); *C12Q 2600/124* (2013.01)

(58) Field of Classification Search
CPC ........................................................ C12Q 1/68
USPC ........................................................ 435/6.12
See application file for complete search history.

(56) References Cited

U.S. PATENT DOCUMENTS

2008/0263730 A1* 10/2008 Andersen ............. C07K 14/415
800/312

\* cited by examiner

*Primary Examiner* — Aaron A Priest

(57) ABSTRACT

The present invention provides a molecular marker C42257 for rapidly identifying genetic sex of *Marsupenaeus japonicus* and applications thereof. The nucleotide sequence of the molecular marker C42257 is shown in SEQ ID NO:1. The nucleotide sequences of the primer pair of molecular marker C42257 used for detection are C42257F: GGGGGACAAACAGAGACA (SEQ ID NO: 2) and C42257R: ATCGGGGTGGATTTAGAA (SEQ ID NO: 3), respectively. The molecular marker C42257 is not affected by the tissue specificity of *M. japonicus* and the environment, and the steps are simple and the results are obvious. The genomic DNA of *M. japonicus* and the primer pair are subjected to PCR reaction and electrophoresis detection. If a target band appears at 183 bp, it is a female *M. japonicus*. The molecular marker can also promote the establishment of the seedling breeding technology of all-female or high-female-ratio *M. japonicus*. Therefore, it has a broad application prospect.

3 Claims, 1 Drawing Sheet

Specification includes a Sequence Listing.

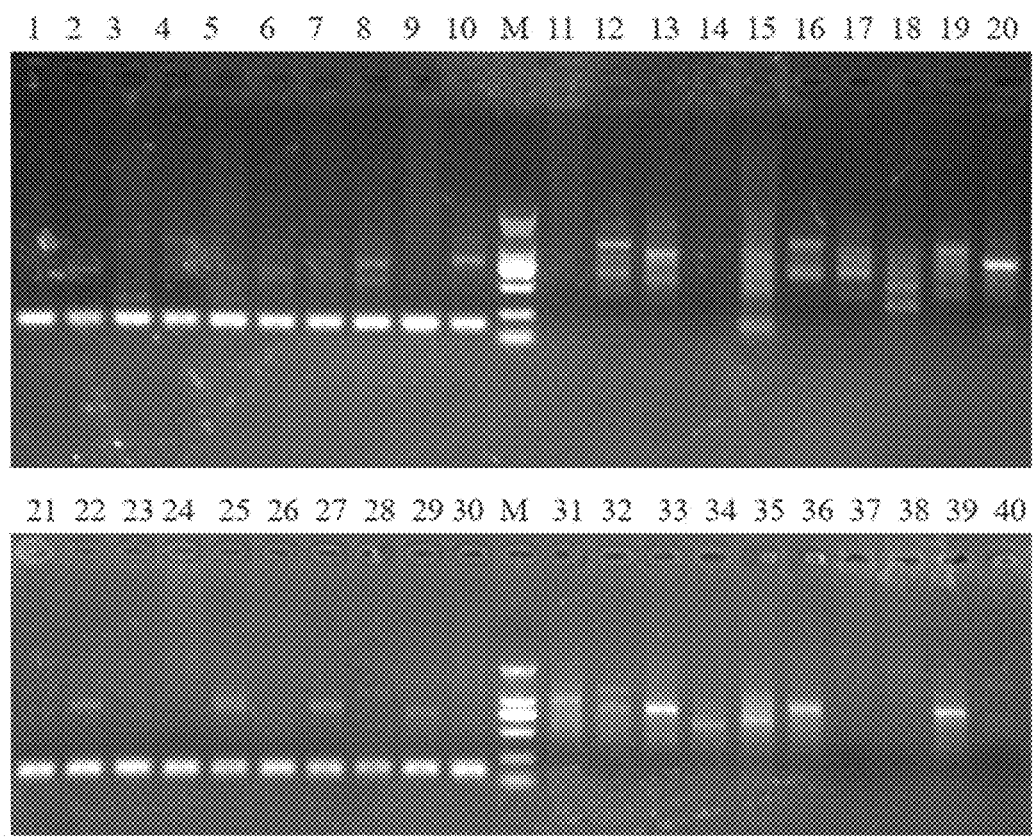

SEQUENCE LISTING

<160> NUMBER OF SEQ ID NOS: 3

<210> SEQ ID NO 1
<211> LENGTH: 350
<212> TYPE: DNA
<213> ORGANISM: Artificial Sequence
<220> FEATURE:
<223> OTHER INFORMATION: used to rapidly identify genetic sex of
      Marsupenaeus japonicas

<400> SEQUENCE: 1

```
aacgaaaaaa ctatcatcgt atacatgggg gacaaacaga gacacattaa tgaaattttc    60
tgatatatat atcagaccaa aaatagatta tggaattacc atttatggaa ctgcaaagaa   120
ccaagaaatg aaaaaaaaca aagactgtat aaaatgcagc tttaagattg accacaggat   180
attctaaatc caccccgata attgctctac aaacattaac aaacaaatcc ccaataacag   240
tcagaatcag agaactagaa tgtaaacaaa tgataaagat attaggaaaa aaagaaaaca   300
tgcccatgaa actattaaca aatttatatg taaaagaata caaccccact              350
```

<210> SEQ ID NO 2
<211> LENGTH: 18
<212> TYPE: DNA
<213> ORGANISM: Artificial Sequence
<220> FEATURE:
<223> OTHER INFORMATION: A forward primer of molecular marker C42257

<400> SEQUENCE: 2

```
gggggacaaa cagagaca                                                  18
```

<210> SEQ ID NO 3
<211> LENGTH: 18
<212> TYPE: DNA
<213> ORGANISM: Artificial Sequence
<220> FEATURE:
<223> OTHER INFORMATION: A reward primer of molecular marker C42257

<400> SEQUENCE: 3

```
atcggggtgg atttagaa                                                  18
```

MOLECULAR MARKER C42257 FOR RAPIDLY IDENTIFYING GENETIC SEX OF *MARSUPENAEUS JAPONICUS* AND APPLICATIONS THEREOF

CROSS-REFERENCE TO RELATED APPLICATIONS

The present application claims the benefit of Chinese Patent Application No. 202110765274.X filed on Jul. 7, 2021, the contents of which are hereby incorporated by reference.

REFERENCE TO SEQUENCE LISTING

A Sequence Listing is submitted as an ASCII formatted text file via EFS-Web, with a file name of "Sequence_Listing.TXT", a creation date of Sep. 2, 2021, and a size of 1,447 bytes. The Sequence Listing filed via EFS-Web is part of the specification and is incorporated in its entirety by reference herein.

TECHNICAL FIELD

The present invention generally relates to the technical field of DNA molecular marker, and particularly to a molecular marker C42257 for rapidly identifying genetic sex of *Marsupenaeus japonicus* (*M. japonicus*) and applications thereof.

BACKGROUND

*Marsupenaeus japonicus* (*M. japonicus*) a belongs to Crustacea, Decapoda, Penaeidae, *Penaeus*. It is widely distributed, ranging from Japan and South-East Asia to East Africa and the Red Sea. *M. japonicus* has the characteristics of rapid growth, strong disease resistance, long survival time under air exposing conditions, and high survival rate of long-distance transportation. Because of its high economic value and high market price, it is an important economical shrimp in coastal areas in China. During aquaculture, the mature female shrimps of *M. japonicus* are larger than the mature male shrimps, therefore, if efficient monosex aquaculture can be realized, the economic efficiency of aquaculture of *M. japonicus* will be improved significantly. However, there is currently no efficient sex control technology for *M. japonicus*.

Molecular markers are genetic markers based on the nucleotide sequence variation of genetic material between individuals, which directly reflects the genetic polymorphisms at the DNA level. Molecular markers have significant advantages. Most of the molecular markers are co-dominant, which is very convenient for the selection of recessive traits. The genome variation is extremely rich, and the number of molecular markers is almost unlimited. The DNAs extracted from different tissues at different stages of biological development can all be used for molecular marker analysis. The molecular marker detection is simple and rapid. The development of molecular markers related to sex identification of *M. japonicus* can realize the monosex breeding of *M. japonicus* and increase the economic incomes of farmers which is of great significance to the aquaculture and breeding of *M. japonicus*.

SUMMARY

The present invention provides a molecular marker C42257 for rapid identification of the genetic sex of *M. japonicus* and applications thereof. In the present invention, through the comparative genomics and bioinformatics analysis methods, sex-specific segments are screened, and a molecular marker C42257 for identifying the genetic sex of *M. japonicus* is obtained. The molecular marker has high identification efficiency and accuracy, and can be used for seedling breeding of all-female or high-female-ratio *M. japonicus*, to facilitate the aquaculture and development of *M. japonicus*.

To achieve the above object, the present invention adopts the following technical solutions:

A primer pair of molecular marker C42257 for detecting and identifying the genetic sex of *M. japonicus*, having nucleotide sequences:

C42257F: GGGGGACAAACAGAGACA (SEQ ID NO:2);
C42257R: ATCGGGGTGGATTTAGAA (SEQ ID NO:3);

The nucleotide sequence of the molecular marker C42257 is shown in SEQ ID NO:1.

The sequence of SEQ ID NO:1 is as follows:

```
AACGAAAAACTATCATCGTATACATGGGGACAAACAGAGACACATT
AATGAAATTTTCTGATATATATATCAGACCAAAAATAGATTATGGAAT
TACCATTTATGGAACTGCAAAGAACCAAGAAATGAAAAAAACAAAGA
CTGTATAAAATGCAGCTTTAAGATTGACCACAGGATATTCTAAATCCA
CCCCGATAATTGCTCTACAAACATTAACAAACAAATCCCCAATAACAG
TCAGAATCAGAGAACTAGAATGTAAACAAATGATAAAGATATTAGGAA
AAAAAGAAAACATGCCCATGAAACTATTAACAAATTTATATGTAAAAG
AATACAACCCCACT
```

The present invention provides a method for rapidly identifying the genetic sex of *M. japonicus* using the primer pair, comprising the following steps:
(1) synthesizing the primer pair C42257F and C42257R;
(2) extracting genomic DNA from *M. japonicus* muscle;
(3) performing PCR amplification with the primer pair C42257F and C42257R using the genomic DNA extracted in step (2) as a template, to obtain PCR amplification products;
(4) performing agarose gel electrophoresis on the PCR amplification product and observing the electrophoresis maps; if a target band of amplification appears at 183 bp in the electrophoresis map, the sex of *M. japonicus* is female, and if no target band of amplification appears at 183 bp in the electrophoresis map, the sex of *M. japonicus* is male.

Further, the PCR amplification reaction conditions in the step (3) are as follows: 94° C., 3 min; 94° C., 30 s, 55° C., 30 s, 72° C., 30 s, repeating 32 cycles; 72° C., 10 min.

Further, the PCR amplification reaction system in the step (3) is: 1 µL of genomic DNA, 5.0 µL of Mix1, 0.2 µL of each of upstream and downstream primers, and sterilized water added to 10 µL.

Compared to the prior art, the present invention has the following advantages and beneficial effects. The molecular marker C42257 for rapid identification of genetic sex of *M. japonicus* provided herein is not affected by the tissue specificity of *M. japonicus* and the environment. The sex identification is simple and rapid and has low requirements for the samples; moreover, the identification result has high accuracy. The present invention can not only be used for identifying the genetic sex of *M. japonicus*, but also can promote the establishment of the seedling breeding technology of all-female or high-female-ratio *M. japonicus*. Therefore, it has a broad application prospect.

BRIEF DESCRIPTION OF THE DRAWINGS

The sole FIGURE shows female-specific marker map of *M. japonicus*, wherein, M: standard molecular weight; 1-10 and 21-30 are for female shrimps; 11-20 and 31-40 are for male shrimps.

DETAILED DESCRIPTION

The technical solutions of the present invention will be further described in detail below in conjunction with specific embodiments. The test methods used in the following examples are conventional unless otherwise specified; the materials and reagents used, unless otherwise specified, are all commercially available reagents and materials.

Example 1

1. DNA Extraction

The DNA of *M. japonicus* was extracted by Novogene, with 30 males and 30 females.

2. Construction of DNA Mixing Pool

The individual DNAs were mixed in equal ratio, to prepare a male and female DNA mixing pool with a concentration of 292.8 ng/μL to 363.3 ng/μL. Each mixing pool contained 30 individuals, which would be used for subsequent experiments.

3. Primer Design

Through the comparative genomics and bioinformatics analysis methods, sex-specific segments were screened, and then sex markers were screened and verified from the sex-specific segments. Using the Primer Premier 5.0 software, primers were designed for sex candidate Contig, the marker DNA sequence (as shown in SEQ ID No. 1, No. C42257) was screened, and the detection primer for this sequence was designed.

The Design Criteria for Primers:

1) Primer annealing temperature: 50° C. to 60° C.

2) Avoid the formation of stable dimers and hairpin structures for primers and between primers.

The information or primers used in this Example is shown in Table 1:

TABLE 1

| Primer Information | | | |
|---|---|---|---|
| Site | Primers Use | Primer Information | Product Length (bp) |
| C42257F | Amplification primer | GGGGGACAAACAGAGACA (SEQ ID NO:2) | 183 |
| C42257R | | ATCGGGGTGGATTTAGAA (SEQ ID NO:3) | |

4. PCR Amplification of Mixed Template and Electrophoresis

PCR amplification was performed with TransGen Biotech's HiFi enzyme using mixed DNA as a template. The PCR reaction procedure was as follows: 94° C., 3 min; 94° C., 30 s, 55° C., 30 s, 72° C., 30 s, 32 cycles; 72° C., 10 min. The PCR system was as follows:

| Reagent | Amount |
|---|---|
| DNA template | 1.0 μL |
| Mix 1 | 5.0 μL |
| Primer (upstream and downstream) | Each 0.2 μL |
| Sterilized water | Added to 10.0 μL |

The mixed template PCR product was subjected to 1% agarose gel electrophoresis. The electrophoresis maps showed that the no target band was amplified in the male mixed DNA pool, while the target band was amplified in the female mixed pool.

5. PCR Amplification and Electrophoresis of Male and Female Individuals

The tissue DNA of 40 *M. japonicus* individuals was extracted as a template for PCR. The PCR primers were C42257F: GGGGGACAAACAGAGACA (SEQ ID NO:2); C42257R: ATCGGGGTGGATTTAGAA (SEQ ID NO:3); the PCR system and PCR amplification reaction procedures were the same as above. After amplification, the individual template PCR products obtained were subjected to 1% agarose gel electrophoresis. The electrophoresis map showed (the sole FIGURE) that, no target band was amplified in all tested male individuals, and the target band was amplified at 183 bp in all tested female individuals.

The results showed that, the molecular marker C42257 obtained in the present invention can accurately identify the genetic sex of *M. japonicus*. The steps were simply described as follows: extracting the genomic DNA of tissues of *M. japonicus*, and performing PCR amplification reaction with the amplification primers C42257F and C42257R of molecular marker using the extracted genomic DNA as a template; performing agarose gel electrophoresis on the PCR amplification product. If a target band of amplification appeared at 183 bp in the electrophoresis map, the sex of *M. japonicus* was female, and if no target band of amplification appeared at 183 bp in the electrophoresis map, the sex of *M. japonicus* was male. The molecular marker C42257 can also be used for seedling breeding of all-female or high-female-ratio *M. japonicus*, to facilitate the aquaculture and development of *M. japonicus*.

The above embodiments are only used to illustrate the technical solutions of the present invention rather than limit them; although the present invention has been described in detail with reference to the foregoing embodiments, those of ordinary skill in the art can make modifications to the technical solutions recorded in the foregoing embodiments or make equivalent replacement on some of the technical features; and these modifications or replacements shall not deviate from the spirit and scope of the technical solutions claimed by the present invention.

What is claimed is:

1. A method for identifying the genetic sex of *Marsupenaeus japonicus*, comprising the following steps:
   (1) synthesizing a primer pair C42257F and C42257R having the following nucleotide sequences:
      C42257F: GGGGGACAAACAGAGACA (SEQ ID NO:2);
      C42257R: ATCGGGGTGGATTTAGAA (SEQ ID NO:3);
   (2) extracting genomic DNA from *Marsupenaeus japonicus* samples;
   (3) performing PCR amplification with the primer pair C42257F and C42257R using the genomic DNA extracted in step (2) as a template, to obtain PCR amplification products; and
   (4) performing agarose gel electrophoresis on the PCR amplification product and observing the electrophoresis maps; if a target band of amplification appears at 183 bp in the electrophoresis map, *Penaeus japonicus* is female, and if no target band of amplification appears at 183 bp in the electrophoresis map, *Penaeus japonicus* is male.

2. The method according to claim 1, wherein the PCR amplification reaction conditions in the step (3) are as follows: 94° C., 3 min; 94° C., 30 s, 55° C., 30 s, 72° C., 30 s, repeating 32 cycles; 72° C., 10 min.

3. The method according to claim 1, wherein the PCR amplification reaction system in the step (3) is: 1 μL of genomic DNA, 5.0 μL of Mix1, 0.2 μL of each of upstream and downstream primers, and sterilized water added to 10 μL.

* * * * *